United States Patent [19]

Jachimowicz

[11] 4,322,530

[45] Mar. 30, 1982

[54] ALKYLATION OF POLYAMINES

[75] Inventor: Felek Jachimowicz, Columbia, Md.

[73] Assignee: W. R. Grace & Co., New York, N.Y.

[21] Appl. No.: 123,823

[22] Filed: Feb. 22, 1980

[51] Int. Cl.³ .............. C07D 241/04; C07D 295/00; C07D 211/00; C07C 85/18

[52] U.S. Cl. ..................... 544/403; 544/358; 544/402; 546/184; 546/194; 546/246; 564/305; 564/306; 564/307; 564/309; 564/336; 564/340; 564/343; 564/346; 564/355; 564/374; 564/378; 564/389; 564/391; 564/395; 564/396; 564/399; 564/401; 564/408; 564/445; 564/467

[58] Field of Search .......... 260/583 R, 585 D, 583 P; 564/467, 305, 336, 408, 445, 467; 544/358, 403; 546/184

[56] References Cited

U.S. PATENT DOCUMENTS

| | | | |
|---|---|---|---|
| 2,381,472 | 8/1945 | Teter | 260/585 D X |
| 2,417,893 | 3/1947 | Teter | 260/585 D X |
| 2,497,310 | 2/1950 | Larson | 260/583 R X |
| 3,513,200 | 5/1970 | Biale | 260/583 R |
| 3,726,926 | 4/1973 | Brown et al. | 260/585 R |
| 3,758,586 | 9/1973 | Coulson | 260/583 R |
| 3,947,458 | 3/1976 | Iqbal | 260/583 R X |
| 4,096,150 | 6/1978 | Berthoux et al. | 564/467 |
| 4,107,079 | 8/1978 | Chevallier et al. | 260/583 R X |
| 4,119,652 | 10/1978 | Knowles et al. | 260/583 R X |
| 4,130,590 | 12/1978 | Hobbs et al. | 260/585 D |
| 4,179,469 | 12/1979 | Imai | 260/583 P X |

FOREIGN PATENT DOCUMENTS

| | | | |
|---|---|---|---|
| 891067 | 3/1962 | United Kingdom | 260/585 D |
| 1072796 | 6/1967 | United Kingdom | 564/467 |
| 1178308 | 1/1970 | United Kingdom | 564/467 |
| 1378185 | 12/1974 | United Kingdom | 564/467 |

OTHER PUBLICATIONS

Houben-Weyl, "Methoden der Organischen Chemie", 4th Ed., vol. 11/1, pp. 994-999, (1957).

Primary Examiner—John Doll
Attorney, Agent, or Firm—Philip M. Pippenger; Howard J. Troffkin

[57] ABSTRACT

A process for alkylating a polyamine by contacting, in a liquid media, a polyamine, an olefinic compound, carbon monoxide, and a hydrogen source in the presence of a catalytic amount of a rhodium atom containing compound selected from metallic rhodium, rhodium salts, rhodium oxides, rhodium carbonyls and ligands thereof at a temperature of from about 50° C. to 250° C. and at a pressure of from about 30 to about 300 atmospheres.

5 Claims, No Drawings

ALKYLATION OF POLYAMINES

BACKGROUND OF INVENTION

The present invention relates to the process of forming alkylated polyamines and, more particularly, to the process of forming fatty polyamines. The subject alkylated polyamines are presently formed by complex synthetic methods such as are described in U.S. Pat. Nos. 3,898,188; 3,899,534; and 4,096,105. The single step catalytic process of the present invention permits the formation of the desired material in an economic manner.

Catalytic aminomethylation of olefins with secondary monoamines, carbon monoxide and hydrogen is well known and was initially taught by Dr. Walter Reppe in *Experiention,* Vol. 5, p. 93 (1949); German Pat. No. 839,800 (1952) and *Liebigs Ann. Chem.,* Vol. 582, p. 148 (1953). The value of the process was, however, of limited value due to the required use of large quantities of toxic iron or nickel carbonyls as the catalyst, the rapid rate of consumption of the catalyst, the slow rate of reaction, and the poor yields obtained. Moreover, the reaction was taught to be restricted to monoolefins and to low molecular weight monoamines.

Aminomethylation of other monoolefins has been carried out in the presence of other metal carbonyls, but the reactions have been found to be non-selective and produce, at best, only moderate yields of amines. For example, U.S. Pat. Nos. 2,422,631 and 3,234,283 disclose that lower olefins, carbon monoxide, hydrogen, and a secondary monoamine will form, in low yields, tertiary amines in the presence of cobalt hydrocarbonyl or dicobalt octocarbonyl as well as certain other cobalt compounds.

More recently, U.S. Pat. Nos. 3,513,200 and 4,096,150 have disclosed the utilization of Group VIII metal compounds as suitable compounds to catalyze the reaction between monoamines and monomeric olefins with hydrogen and carbon monoxide to form low molecular weight tertiary amines. The above reactions are generally plagued by the formation of significant amounts of byproducts and by the required use of hydrogen which is both unsafe and expensive. The reactions are, therefore, not deemed suitable for the formation of specific compounds.

Alkylated polyamines and products derived therefrom are highly desired compounds known to be useful as surfactants, flocculating agents, softeners and as a desired component of some coating compositions. Conventional methods of forming such alkylated polyamines have been difficult and costly. It is highly desired to find an economical process for forming alkylated polyamines and especially for the formation of fatty amines.

SUMMARY OF THE INVENTION

The present process is directed to a one-step, economical method of forming alkylated polyamines and, more particularly, fatty polyamines by contacting, in a liquid media, a polyamine, an olefinic compound, carbon monoxide, and water in the presence of a catalytic amount of a rhodium compound selected from metallic rhodium, rhodium salts, oxides, carbonyls, phosphines or ligands. The reaction is carried out in an inert solvent at temperatures of from 50° to 250° C. and at a pressure of from about 30 to about 300 atmospheres.

DETAILED DESCRIPTION

The subject invention is directed to a new and novel one-step, catalytic method of alkylating a polyamine by contacting, in an inert solvent, a compound having a multiplicity of primary and/or secondary amine groups, a monoolefin, water and carbon monoxide in the presence of certain rhodium compounds as the catalyst, as more completely described herein below.

Organic compounds having at least two amino nitrogens therein which form either a primary or a secondary amino group are suitable in the subject process. These compounds are referred to in the instant disclosure as "polyamines" or "polyamine" and can be represented by the general formula

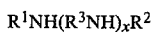

$$R^1NH(R^3NH)_xR^2$$

wherein $R^1$ and $R^2$ each separately represent a hydrogen atom or a hydrocarbyl such as an alkyl, aryl, alkaryl or aralkyl which, preferably, has from one to twelve carbon atoms or $R^1$ and $R^2$ together represent an alkylene group, $R^3$ is an alkylene group and x is a whole integer of 1 or greater. Generally, when $R^1$ or $R^2$ is a hydrocarbyl it is preferred that each have from one to twelve carbon atoms such as methyl, ethyl, t-butyl, cyclopentyl, phenyl, tolyl and the like. Further, the $R^3$ alkylene group can contain any number of carbon atoms and, preferably has from one to twelve carbons such as methylene, ethylene, tetramethylene, hexamethylene, phenylene, biphenylene, tetramethyl phenylene and the like. When $R^1$ and $R^2$ are together an alkylene, $R^1$, $R^2$ and $R^3$ should not be greater than six carbon atoms in combination.

Examples of such polyamines include ethylenediamine, propylene diamine, hexamethylene diamine, diethylenetriamine, triethylene tetraamine, trimethylenetriamine, N,N¹-dimethyl ethylenediamine, N,N¹-dibutyl ethylenediamine, N-methyl, N¹-ethyl ethylenediamine, N,N¹-diphenyl ethylenediamine, phenylene diamine, piperazine, polyethylenimine and the like.

The subject process requires the use of polyamine compounds which compounds have been found uniquely different from monoamines used in the processes of the prior art. The subject process including the required use of the subject polyamines yields desired products in a simple manner and in high yields.

The olefinic unsaturated compounds which are useful in the present invention are olefinic compounds having from 2 to about 20 carbons and can be represented by the general formula.

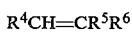

$$R^4CH=CR^5R^6$$

wherein each $R^4$, $R^5$ and $R^6$ represents hydrogen or a $C_1$ to $C_{18}$ hydrocarbyl including alkyl, aryl, alkaryl, aralkyl, cycloalkyl and substituted derivatives in which the substituted group is inert to the reaction and may be selected from carboyl, tertiary amino, hydroxy, alkoxy, thio and the like. Further $R^4$ and $R^5$ combined can represent a $C_2$–$C_6$ alkylene group or a substituted alkylene group wherein the substituted groups are the same as described above or a $C_1$ to $C_{14}$ hydrocarbyl group.

Examples of useful olefins are the hydrocarbon olefins such as ethylene, propylene, butene-1, butene-2, isobutylene, pentene-2, 2-methylbutene-1, hexene-1, 3-ethylhexene-1, octene-3, 2-propylhexene-1, decene-2, 4,4'-dimethyl nonene-1, dodecene-1, 6-propyldecene-1, tetradecene-5, 7-amyldecene-3, hexadecene-1, 4-ethyltridecene-2, octadecene-1, 5,5-dipropyldodecene-3, eicosene-7, etc. Of these the aliphatic hydrocarbon olefins having from about 10 to 20 carbons are preferred and most preferred are the alpha olefins having terminally unsaturated carbons when desiring to form fatty polyamines by the process of the subject invention.

Other olefins that can be used include vinyl cyclohexane allyl cyclohexane, styrene, p-methyl styrene, alpha methyl styrene, beta methyl styrene, p-vinyl cumene, beta vinyl naphthalene, 1,2-diphenyl ethylene, allyl benzene, 6-phenylhexene-1, 1,3-diphenylbutene-1, 3-benzoheptene-3, o-vinyl, p-xylene, crotonyl alcohol, allyl carbinol, beta-allylethyl alcohol, allylmethylpropylcarbinol, allylphenol, etc.

Cycloalkenes and their substituted derivatives include cyclobutene, cyclopentene, cyclohexene, methylcyclohexene, amylcyclopentene, cycloheptene, cyclooctene, cyclodecene, etc.

The particular polyamine and the particular olefinic compound to be used will depend on the resultant product desired.

The equivalent ratio of olefinic bond to each primary or secondary amino nitrogen contained in the reaction zone should be from about 1.05 to 3 with from 1.05 to 2 being preferred. It is sometimes suitable to have the olefinic bond containing compound present in large excess and act as liquid media or at least a part of the liquid media in which the process is carried out.

The alkylation of the polyamine has been found to readily occur when the chosen polyamine and the chosen olefinic compound, as described above, are contacted with carbon monoxide and water in the presence of a catalyst described herein below. It has been unexpectedly found that water acts as an effective source of hydrogen in the subject process, does not have the detrimental safety problems normally associated with hydrogen gas and, in general, enhances the yield of alkylated product. Water can be used in combination with hydrogen gas as the hydrogen source although poorer yields and safety problems complicate the reaction. Water alone is, therefore, the preferred hydrogen source.

The reaction is performed under liquid phase conditions. Any suitable organic liquid can be employed which is inert to the reaction conditions, the reactants, the catalyst and the products. Examples of suitable solvents that can be used in accordance with this invention include hydrocarbons such as the aromatics, aliphatics or alicyclic hydrocarbons, ethers, esters, etc.

Examples of suitable hydrocarbons that can be employed as the solvent include aromatic hydrocarbons such as benzene, toluene, xylene, ethyl benzene, tetralin, etc.; aliphatic hydrocarbons such as butane, pentane, isopentane, hexane, isohexane, heptane, octane, isooctane, naphtha, gasoline, kerosene, mineral oil, etc.; alicyclic hydrocarbons, such as cyclopentane, cyclohexane, methylcyclopentane, decalin, indane, etc.

Ethers can also be employed as the reaction solvent, such as diisopropyl ether, di-n-butyl ether, ethylene glycol diisobutyl ether, methyl o-tolyl ether, ethylene glycol dibutyl ether, diisoamyl ether, methyl p-tolyl ether, methyl m-tolyl ether, dichloroethyl ether, ethylene glycol diisoamyl ether, diethylene glycol diethyl ether, ethylbenzyl ether, diethylene glycol diethyl ether, diethylene glycol dimethyl ether, ethylene glycol diethyl ether, ethylene glycol diphenyl ether, triethylene glycol diethyl ether, diethylene glycol di-n-hexyl ether, tetraethylene glycol dimethyl ether, tetraethylene glycol dibutyl ether, etc.

Various esters can also be employed as the solvent, such as ethyl formate, methyl acetate, ethyl acetate, n-propyl formate, isopropyl acetate, ethyl propionate, n-propyl acetate, sec-butyl acetate, isobutyl acetate, ethyl-n-butylate, n-butyl acetate, isoamyl acetate, n-amyl acetate, ethyl formate, ethylene glycol diacetate, glycol diformate, cyclohexyl acetate, furfuryl acetate, isoamyl n-butyrate, diethyl oxalate, isoamyl isovalerate, methyl lenzoate, diethyl malonate, valerolactone, ethyl benzoate, methyl salicylate, n-propyl benzoate, n-butyl oxalate, n-butyl benzoate, diisoamyl phthalate, dimethyl phthalate, diethyl phthalate, benzyl benzoate, n-butyl phthalate, etc. A preferred class of ester solvents include the lactones, e.g., butyrlactone valerolactone and their derivatives having lower ($C_1$–$C_5$) alkyl substituents.

Alcohols can be employed as the reaction solvent. Preferably the alcohol is a $C_1$ to $C_8$ alcohol and can be a primary alcohol, such as methanol, ethanol, n-propanol and the like; secondary alcohols, such as isopropanol, 1-methyl pentanol and the like; and tertiary alcohols, such as t-butyl and t-amyl alcohols.

Tertiary amines can also be employed as the reaction solvent, the nitrogen atom, by definition, being substituted with three hydrocarbyl groups which are inert with respect to the reaction, such as, for example, alkyl, aryl, alkaryl, aralkyl groups and the like. Examples of suitable tertiary amines include trimethylamine, triethylamine, tripopylamine, triisobutylamine, trihexylamine, triheptylamine, triamylamine, dibenzyl ethylamine, dibutyl ethylamine, dimethyl pentylamine, diphenyl ethylamine, diphenyl methylamine, dimethyl aniline, pyridine, dimethyl pyridine, methoxy pyridine, methyl pyrrolidine, N-ethyl pyrrolidine, N-methyl piperidine and the like. The preferred solvents are the teritary amines and, especially, trimethylamine pyridine, N-alkyl, substituted pyrrolidine and its derivatives or piperidine.

The particular solvent to be used will depend on its ability to remain in the liquid state at both ambient and at reaction conditions to facilitate the mixing of the components, its solvating ability with respect to at least some of the reactants, and its ease of handling, as can be readily determined by the artisan.

The reaction is performed under relatively mild conditions including temperatures from about 80° to about 250° C.; preferably from about 100° to about 200° C. Sufficient pressure should be used to maintain the reaction medium in a liquid phase. The reaction is carried forth at super-atmospheric pressure such as from about 30 to about 300 atmospheres and, preferably, from about 30 to 100 atmospheres. Since the reaction is exothermic, the temperature can be maintained by suitable cooling of all or a portion of the reaction zone contents. The pressure can be maintained by the pressure of the carbon monoxide and, when used, hydrogen supplied to the reaction zone. If desired, a suitable inert gas, such as nitrogen, can also be charged to the reaction zone to supplement the partial pressures of the reaction gases.

The ratio of the reactants can be widely varied. The mole ratio of carbon monoxide to the hydrogen source should be at least about 3:1. Higher ratios, such as 5:1 or above, are preferred. The carbon monoxide can be used in excess to form sufficient pressure required in the reaction zone, as described above. The mole ratio of hydrogen source to amino group can be varied from about 1:10 to 10:1 with from about 1:3 to 3:1 being preferred. Finally, the ratio of olefinic bond compound to the combined primary and secondary nitrogen atoms of the polyamine reactant should be such that the molar ratio should be at least from 1 to 1 and preferably from at least 1 to 2.

The catalyst required to cause the formation of the desired alkylated polyamines comprises rhodium compounds selected from elemental rhodium, rhodium salts, rhodium oxides, rhodium carbonyls, rhodium ligands as described herein below. The preferred catalysts are formed from rhodium compounds in which the rhodium atom is the plus one valence state. The exact chemical and physical composition of the entity which acts as the catalyst for the subject reaction is not known with certainty because of the possible restructuring and/or interaction of the rhodium compound used and the reactants contained in the reaction zone. Whether the rhodium compounds described herein directly act as the catalyst or as the precursor for the catalyst entity which causes the presently desired aminomethylation is immaterial. The subject rhodium compounds will be referred herein as the "catalyst" as they have unexpectedly been found to aid directly and/or indirectly in the formation of desired alkylated polyamines by the present one-step process and to give the desired product in high yields.

The rhodium compounds which are useful in catalyzing the subject reaction must have some degree of solubility in the liquid media in which the subject aminomethylation is to take place. The choice of liquid media and/or catalyst to be used in a particular reaction so that the catalyst has some degree of solubility can be readily determined by those skilled in the art using conventional methods.

The catalyst found useful in the subject process can be a rhodium salt of an inorganic acid such as, for example rhodium chloride, rhodium nitrate, rhodium sulfate, rhodium perchlorate and the like or of an organic acid such as rhodium acetate and the like. The rhodium salts are well known commercial products formed conventionally by the reaction of rhodium oxide with an acid. The salt can be used in its anhydrous state or as a hydrated salt. The hydrated salts being preferred.

The catalyst of the subject process can be rhodium ligand. The ligand can be formed in coordination with rhodium in any one of its valence states; that is of zero or plus 1, 2 or 3. The ligand moiety is formed from chemical moieties which contain unshared electrons such as atoms selected from nitrogen, oxygen, phosphorus or sulfur or which contains unsaturation. The ligand can be in the form of a carbonyl; an olefin such as ethylene, butene and the like; diolefines such as norbornadiene, cyclooctadiene-1,5 and the like; aliphatic, aromatic, aryl or aliphatic phosphites, such as triethyl phosphite, tributyl phosphite, trimethyl phosphite, triphenyl phosphite, dimethyl phenyl phosphite, tritolyl phosphite, tribenzyl phosphite, ditolyl phenyl phosphite, and the like; aliphatic and cyclic ethers such as dimethyl and diethyl oxide, dioxane, dialkyl ether glycols, acetyl acetone and the like; primary, secondary, and tertiary amines which contain alkyl, aryl, alkaryl, aralkyl, cycloalkyl groups or mixtures thereof such as trimethyl amine, diethyl amine, toluidine and the like; heterocyclic basis such as pyridine, bypyridine and the like; ammonia; sulfides such as dialkyl, diaryl, alicyclic heterocyclic sulfides and the like; and mixtures of said ligand components with rhodium. When the ligand is formed from uncharged ligand components with charged rhodium, the compound is formed into a stable neutral state with an anion such as chloride perchlorate, nitrate, hexaflourophosphate and the like.

The ligand may be added directly to the reaction medium and/or introduced into the medium as a complex of the ligand precursor with the rhodium salt, chelate, hydride or carbonyl. For example, the appropriate precursor of the desired ligand can be introduced into the reaction zone with a rhodium precursor such as, for example rhodium oxide, a rhodium carbonyl as dirhodium dichloro tetracarbonyl, and the like.

The catalyst materials which are useful in the subject process can be generically described by the formula:

$Rh_r[A]_a[B]_b[C]_c$ wherein A represents an anion of an inorganic salt such as nitro, sulfo, halo, especially chloro, and the like; B represents a chemical moiety containing an entity having at least one pair of unshared electrons such as carbonyl, olefin, phosphite, ethers, amines, sulfides and mixtures thereof; C represents an anion capable of forming a neutral compound, such as trifluorophosphite, a, b and c each represent a whole integer including 0 and r represents a whole integer of 1 or greater.

The catalyst material can be added directly to the reaction medium either prior or subsequent to the introduction of the required reactants. The ligand catalyst described above can be added directly or as a complex of the ligand precursor such as a rhodium salt, hydride or carbonyl as, for example, dirhodium dichloro tetracarbonyl and the like.

The rhodium compound useful in the present invention can be metallic rhodium. The metallic rhodium can be in any form such as a powder, ribbon, or coated on an inert support. The inert support can be any conventional catalytic support as are well known such as formed from alumina, carbon, or a metal oxide, as, for example, an alkali or alkaline earth metal oxide and the like. The coating of metallic rhodium can be done by vapor disposition or other conventional methods and should be present in from about 2 to 8 percent by weight of the inert support. Although metallic rhodium has, per se, substantially no solubility in the liquid media contemplated for use, it is believed that metallic rhodium reacts with one or more of the required components in the reaction zone to form a product which is sufficiently soluble to cause the desired aminomethylation to proceed. The metallic rhodium is, most probably, a precursor for the actual catalytic rhodium compound required of the subject process.

The catalyst has been found to be effective to cause the desired alkylation of a polyamide compound as described above when used in a molar ratio of rhodium atom to olefin bond of from about $1 \times 10^{-4}$ to $2.5 \times 10^{-3}$ with preferably from about $1 \times 10^{-4}$ to $1 \times 10^{-3}$. The most preferred range from both effectiveness and economy is from $5 \times 10^{-4}$ to $2 \times 10^{-3}$. Although greater amounts of catalyst can be used, such has not been found required.

The rhodium catalysts found useful in the subject invention may be used in combination with other metal complexes which are known to cause aminomethylation as for example iron or cobalt carbonyl complexes and the like although poorer results are normally achieved. The rhodium catalyst should, therefore, be the sole or major catalyst used in the subject reaction.

The preferred rhodium catalysts are those which have rhodium in its plus 1 valence state and has been complexed with a carbonyl or diolefin or both. Water is the preferred hydrogen source.

The reaction is carried out in a vessel which is preferably adapted for gas injection, agitation and heating. The liquid media is first introduced followed by the olefinic containing compound, the polyamine and the rhodium catalyst. Water can be added along with the other components. When the reaction is carried out under elevated temperature and pressure, the vessel is closed and charged to a specific partial pressure with carbon monoxide. Any additional pressure required can be obtained with an inert gas, such as nitrogen. The reactor and its contents are maintained at the desired elevated temperature of from about 100° C. to 200° C. for a period of time from about 15 minutes to about 10 hours with from about 30 minutes to 5 hours being sufficient and preferred in most instances. The vessel is then cooled down, where appropriate, degassed and the alkylated polyamine is recovered and tertiary amino nitrogen is determined by standard analytical techniques. The primary product is tertiary amine.

The subject process has been found useful in forming fatty amines, especially odd carbon atom containing fatty amines. The later material are normally extremely difficult to produce by known techniques. In forming fatty amines one uses a $C_{12}$ to $C_{20}$ monoolefin compound such as disclosed herein above. When odd carbon atom containing fatty amine is desired one can readily form the same by using an even number carbon atom containing monoolefin having from twelve to twenty carbon atoms as the olefin reactant.

The following examples are for illustrative purposes only and are not meant to be a limitation on the subject invention except as indicated in the appended claims. All parts and percentages are by weight except where otherwise indicated.

EXAMPLE I 10.8 g. of piperazine, 25.3 ml of cyclohexene, 9 ml of water and 25 ml of N-methyl piperidine were placed in a 150 ml stainless steel reactor. 370 mg of commercially obtained rhodium norbornadiene tris (dimethylphenylphosphine) hexafluorophosphine, $[Rh(NBD)(CH_3)_2P(C_6H_5)_3]^- PF_6^+$ was then placed in the reactor. The reactor was sealed and pressurized at ambient temperature of 25° C. with carbon monoxide to 1000 psi. The reactor was placed in an oil shaker bath for 6 hours at 140° C. and then cooled to ambient temperature. The contents were removed and washed with diethyl ether and water. The ether washings were collected, and evaporated to dryness. The solid product was recrystalized with methanol. The product (70% yield) was identified by H-NMR to be the desired tertiary diamine $^{13}C = 77.52\%$ M = 10.10% H = 12.3%.

EXAMPLE II

The process of Example I above was repeated using 134 ml of cyclohexene, 50 g of piperizine, 42 ml of water, 200 ml of N-methyl piperidine and 400 mg of the same rhodium catalysts prepared in accordance with the procedure of Schrock and Osborn, JACS, 93 2397 (1971). The reactants were placed in a 2 l stainless steel reactor which was sealed and pressurized with 1000 psi of CO at ambient temperature. The reaction was carried out at 150° C. for 8 hours. The recovered tertiary diamine product (yield 70%) was identified by H-NMR.

EXAMPLE III

Several runs were made using different rhodium catalysts. In each of the runs $1.06 \times 10^{-2}$ mole of cyclohexene, $5.3 \times 10^{-3}$ mole of piperazine, $1.06 \times 10^{-2}$ water were placed in 30 ml stainless steel reactors with 2 ml of N-methyl piperidine and selected rhodium catalysts, as indicated below. Each of the catalysts were used in an amount such that the moles ratio of olefin to rhodium atom was 500. The reactors were sealed, pressurized with 1000 psi of carbon monoxide and placed in a shaking oil bath for 7 hours at 160° C. and then cooled to room temperature. The contents were removed and the recovered product was analyzed by gas-liquid chromatography internal standard methods. Each run gave the following percent conversion to tertiary amine:

$Rh_6(CO)_{16}$—95%;
$RhCl_3(C_5H_5N)_3$—92%;
$Rh(CO)_2(C_5H_7O_2)$—94%;
$[RhCl(C_7H_8)]_2$—94%

EXAMPLE IV

The procedure of Example III was repeated except that ethanol was used as solvent in lieu of N-methyl piperidine with the catalyst of $[RhCl(C_7H_8)]_2$. The recovered product was analyzed by gas-liquid chromatography and determined to be tertiary amine in 94% yield.

EXAMPLE V

The procedure of Example III is repeated except that the reactant piperazine is substituted with an equivalent amount of commercially obtained phenylene diamine, N,N'-diphenylethylenediamine and hexamethylene diamine. The product obtained in each case is analyzed by standard technique and found to give conversions similar to that obtained in Example III.

While the invention has been described in connection with certain preferred embodiments, it is not intended to limit the invention to the particular forms set forth, but, on the contrary, it is intended to cover such alternatives, modifications and equivalents as defined by the appended claims.

What is claimed is:

1. A process of alkylating a polyamine comprising contacting, in a liquid media, a mixture of a polyamine having the formula:

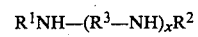

$$R^1NH-(R^3-NH)_xR^2$$

wherein $R^1$ and $R^2$ each represent hydrogen of a hydrocarbyl radical, $R^3$ represents an alkylene radical and x is a whole integer, an olefin having the formula:

$$R^4CH=CR^5R^6$$

wherein $R^4$, $R^5$ and $R^6$ each represent hydrogen, hydrocarbyl or a substituted hydrocarbyl, carbon monoxide and water as the hydrogen source wherein the reactants in the reaction mixture are present in amounts such that the molar ratio of olefinic groups to amino groups is at least 1:1, the molar ratio of the hydrogen source to the amino groups is from 1:10 to 10:1; and the molar ratio of carbon monoxide to hydrogen source is at least about 3:1; heating said mixture to a temperature of from about 50° to 250° C. under a pressure of from about 30 to about 300 atmospheres in the presence of a catalytic amount of a rhodium atom containing compound selected from metallic rhodium, rhodium salt, rhodium carbonyl, rhodium oxide and ligands thereof for a sufficient period of time to cause the formation of alkylated polyamine product; and recovering the alkylated polyamine product.

2. The process of claim 1 wherein the rhodium compound contains a ligand moiety, said ligand moiety contains at least one atom selected from oxygen, sulfur, phosphorus or nitrogen or olefinic unsaturation.

3. The process of claim 1 wherein the catalyst is a rhodium atom containing compound having the general formula:

$$Rh_r[A]_a[B]_b[C]_c$$

wherein A represents halo, nitro, sulfo; B represents a chemical moiety containing at least one pair of unchared electrons selected from carbonyls, olefins, phosphite, ethers, amines, sulfides and mixtures thereof; and C is a neutral compound forming anion and a, b and c each represent a whole integer including 0 and r represents a whole integer of 1 or greater.

4. The process of claim 1, wherein $R^1$ and $R^2$ together form an alkylene radical and $R^1$, $R^2$ and $R^3$ combined have up to six carbon atoms.

5. The process of claim 1 wherein the rhodium atom containing catalyst is present in the reaction zone in an amount that the ratio of rhodium atom to olefinic group is from $1 \times 10^{-4}$ to $2.5 \times 10^{-3}$.

* * * * *